(12) United States Patent
Razzetti et al.

(10) Patent No.: US 7,420,091 B2
(45) Date of Patent: Sep. 2, 2008

(54) PROCESS FOR THE PREPARATION OF TOLTERODINE

(75) Inventors: Gabriele Razzetti, Sesto S. Giovanni (IT); Simone Mantegazza, Milan (IT); Roberto Rossi, Pavia (IT); Pietro Allegrini, San Donato Milanese (IT)

(73) Assignee: Dipharma S.p.A., Mereto di Tomba (IT)

( * ) Notice: Subject to any disclaimer, the term of this patent is extended or adjusted under 35 U.S.C. 154(b) by 0 days.

(21) Appl. No.: 12/000,587

(22) Filed: Dec. 14, 2007

(65) Prior Publication Data

US 2008/0097127 A1    Apr. 24, 2008

Related U.S. Application Data

(62) Division of application No. 11/356,953, filed on Feb. 21, 2006, now Pat. No. 7,335,793.

(30) Foreign Application Priority Data

Feb. 18, 2005   (IT) .................. MI2005A0249

(51) Int. Cl.
*C07C 211/00* (2006.01)
*C09B 11/02* (2006.01)
(52) U.S. Cl. .................................... 564/316
(58) Field of Classification Search ............ 564/316
See application file for complete search history.

*Primary Examiner*—Yvonne Eyler
*Assistant Examiner*—Kellette Gale
(74) *Attorney, Agent, or Firm*—Young & Thompson

(57) ABSTRACT

A novel process for the preparation of tolterodine, i.e. (R)—N, N-diisopropyl-3-(2-hydroxy-5-methylphenyl)-3-phenyl-propanamine, in the racemic form, as well as intermediates useful for its preparation.

2 Claims, No Drawings

PROCESS FOR THE PREPARATION OF TOLTERODINE

FIELD OF THE INVENTION

The present invention relates to a novel process for the preparation of tolterodine, i.e. N,N-diisopropyl-3-(2-hydroxy-5-methylphenyl)-3-phenylpropanamine, in the racemic form, as well as intermediates useful for its preparation.

Tolterodine, having formula (I),

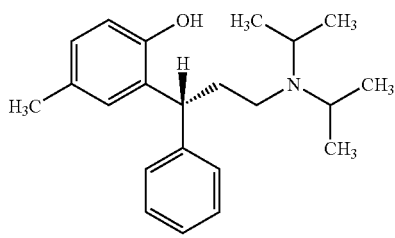

is a medicament useful in the treatment of urinary incontinence, disclosed in EP 325 571.

TECHNOLOGICAL BACKGROUND

A number of processes for the preparation of tolterodine are known. Many of them make use of starting products hardly available or the synthesis of which requires a number of steps, so that their preparation is troublesome. By way of example, U.S. Pat. No. 5,922,914 and EP 325 571 employ the intermediate 4-phenyl-chroman-2-ol. There is therefore the need for an alternative process for the preparation of racemic tolterodine, which makes use of easily available or obtainable starting products and operative conditions well suited to the industrial production, thereby decreasing costs.

SUMMARY OF THE INVENTION

It has now surprisingly been found that a compound having formula (II)

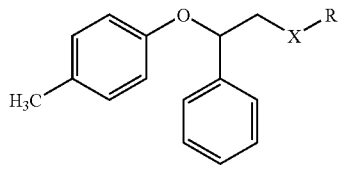

wherein X is —CH$_2$— and R is —N(isopropyl)$_2$; or

X is =CO and R is —N(isopropyl)$_2$ or —OR$_1$ wherein R$_1$ is an aryl or a straight or branched C$_1$-C$_6$ alkyl group, optionally substituted with phenyl, which can be prepared from easily available products, can be transformed into tolterodine or intermediates useful for its preparation by reaction with an acid agent. Similarly, tolterodine or the same above intermediates can be obtained by reacting a compound of formula (III)

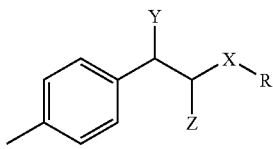

wherein Y is a group able to provide a benzylic carbocation and Z is hydrogen or Y and Z, taken together, complete a double bond; and X and R are as defined above, with p-cresol and an acidic agent.

The novel process for the preparation of racemic tolterodine allows to avoid using hardly available starting products, reactants and reaction conditions troublesome for the industrial production. The main advantages of the process of the invention will be apparent from the following disclosure.

DETAILED DISCLOSURE OF THE INVENTION

The object of the invention is a process for the preparation of tolterodine or a pharmaceutically acceptable salt thereof, comprising:

A) reacting a compound of formula (II)

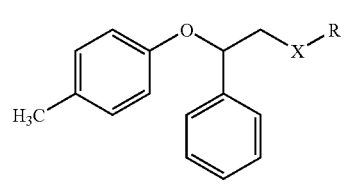

in which when X is —CH$_2$— then R is —N(isopropyl)$_2$; or when X is =CO then R is —N(isopropyl)$_2$ or —OR$_1$, wherein R$_1$ is an aryl or a straight or branched C$_1$-C$_6$ alkyl group, optionally substituted with phenyl; with an acidic agent; or B) reacting a compound of formula (III)

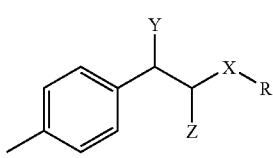

wherein Y is a group able to provide a benzylic carbocation and Z is hydrogen or Y and Z, taken together, complete a double bond; and X and R are as defined above, with p-cresol and an acidic agent; to obtain, respectively, when in a compound of formula (II) or (III)

a) X is —CH$_2$— and R is —N(isopropyl)$_2$, a compound of formula (I)

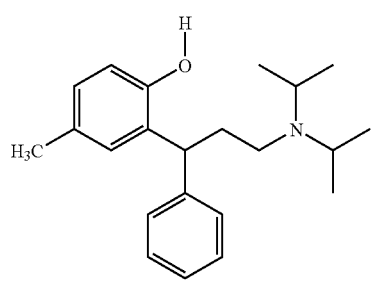

i.e. tolterodine free base; or when b) X is =CO and R is —N(isopropyl)₂, a compound of formula (IV)

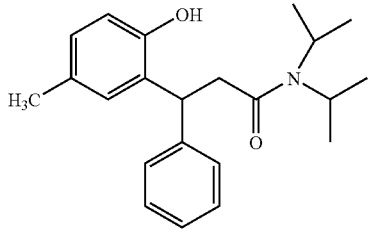

which by reduction yields tolterodine free base; or when c) X is =CO and R is a —OR₁, group wherein R₁ is as defined above, a compound of formula (V)

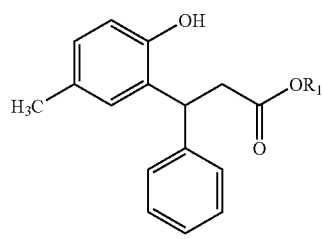

which is converted to tolterodine free base; and, if desired, converting tolterodine free base into a pharmaceutically acceptable salt thereof.

An aryl group is for example phenyl or naphthyl, preferably phenyl.

A $C_1$-$C_6$ alkyl group is preferably a $C_1$-$C_4$ alkyl group, such as methyl, ethyl, propyl, isopropyl, butyl or tert-butyl. When substituted with phenyl, this is for example benzyl or phenylethyl.

Y as a group able to provide a benzylic carbocation is for instance a hydroxy group or a reactive derivative thereof, such as a $C_1$-$C_6$ alkyl or aryl ether, a $C_1$-$C_6$ alkyl or aryl carboxylate, a $C_1$-$C_6$ alkyl or aryl sulfonate, a trifluoromethansulfonate, a sulphate, a nitrate, a phosphate, a $C_1$-$C_6$ alkyl or aryl phasphonate; an halogen atom, e.g chlorine, bromine, fluorine or iodine.

A tolterodine pharmaceutically acceptable salt can be a salt with a physiologically acceptable organic or inorganic acid, such as hydrochloric, hydrobromic, fumaric or tartaric acids.

An acidic agent is typically a Lewis acid, preferably a mineral or organic acid or an aqueous solution thereof, such as hydrochloric, hydrobromic, phosphoric, sulfuric, polyphosphoric, trifluoroacetic, methanesulfonic, ethanesulfonic or p-toluenesulfonic acids; preferably polyphosphoric, sulfuric, methanesulfonic or p-toluenesulfonic acids; in particular polyphosphoric acid or approx. 60% sulfuric acid aqueous solution.

The rearrangement of a compound of formula (II) or process variant B) above, to obtain, according to alternatives a), b) or c), tolterodine free base, a compound of formula (IV) or of formula (V) as defined above, respectively, can optionally be effected in the presence of a solvent. A solvent can be an organic solvent, typically, an aromatic hydrocarbon such as toluene or xylene; a chlorinated solvent, such as dichloromethane, dichloroethane, tetrachloroethylene, chlorobenzene or dichlorobenzene; or a mixture of two or more, preferably two or three, of said organic solvents; or a mixture of one or two thereof with water. An excess of the acidic agent solution itself can act as solvent. The stoichiometric ratio of a compound of formula (II) or (III) to the acidic agent approx. ranges from 0.5 to 50, preferably approx. from 1 to 5. The reaction can be carried out at a temperature approx. ranging from 0° C. to the reflux temperature of the reaction mixture, preferably from 20° C. to 30° C.

The stoichiometric ratio between a compound of formula (III), as defined above, and p-cresol is approximately from 1:1 to 1:2, preferably from 1:1 to about 1:1.5.

The reduction of a compound of formula (IV) to obtain tolterodine free base can be carried out according to known methods, for example with a metal hydride complex, such as $LiAlH_3$ as disclosed in EP 325 571.

The conversion of a compound of formula (V) to tolterodine free base can be carried out with known methods, for example according to EP 325 571, by a process comprising:

a') protection of the phenol group, b') reduction of the ester function to primary alcohol and its conversion to a leaving group; and c') reaction with diisopropylamine and cleavage of the protecting group.

A leaving group can be for example chlorine, bromine, iodine, methanesulfonyl, p-toluenesulfonyl, preferably methanesulfonyl and p-toluenesulfonyl.

The process of the invention to obtain tolterodine is preferably carried out according to variant A), alternative a) of the process described above, in particular in the absence of solvent, preferably by reaction with an acid agent selected from approx. 60% sulphuric acid aqueous solution, polyphosphoric, methansulfonic and p-toluenesulfonic acids, in particular from about 60% sulphuric acid aqueous solution and polyphosphoric acid.

The conversion of tolterodine free base to a pharmaceutically acceptable salt thereof can be carried out according to known methods.

A compound of formula (II) in which X is —CH₂— and R is —N (isopropyl)₂, which can optionally be isolated, can be obtained by reacting p-tolyloxy benzyl ether, having formula (VI), with a metallating agent and an amine of formula (VII) Lg-(CH₂)₂—N(isopropyl)₂ wherein Lg is a leaving group.

The reaction can be schematized as follows:

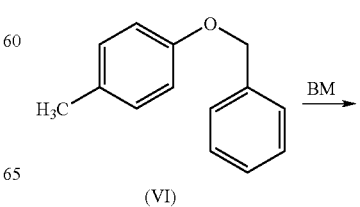

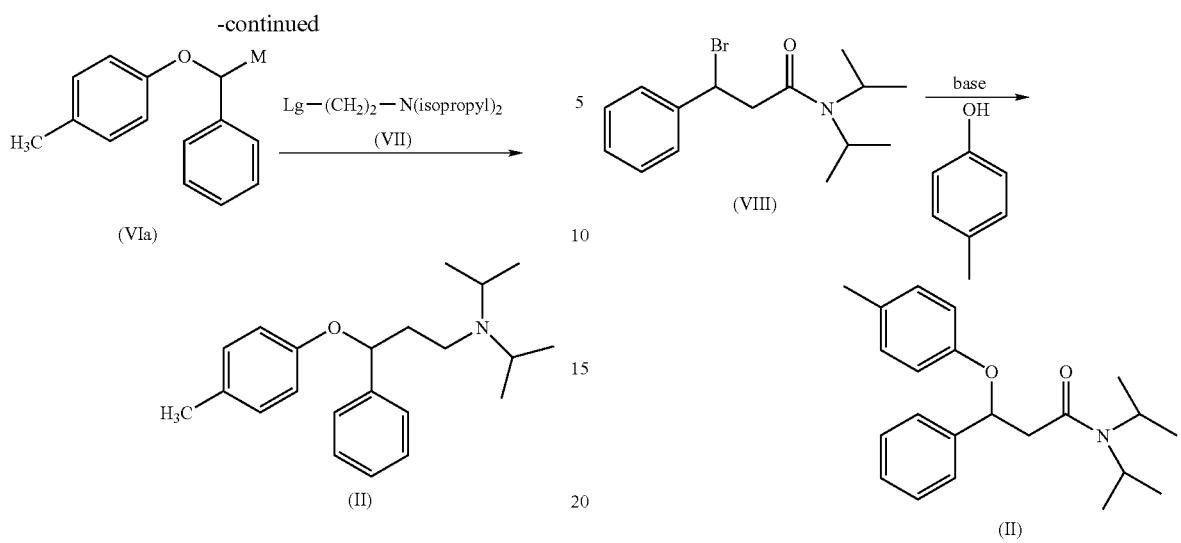

A metallating agent is for example a compound of formula B-M, wherein M is an alkali or alkaline-earth metal, such as sodium, lithium, potassium or magnesium and B is a strong organic or inorganic base. Preferred examples of bases such are butyl lithium, magnesium diisopropylamide, lithium diisopropylamide, lithium hexamethyldisilylazide, potassium tert-butoxide, sodium or potassium hydride, more preferably butyl lithium.

In an amine of formula (VII) the leaving group Lg can be, for example, chlorine, bromine, iodine, methanesulfonyl, p-toluenesulfonyl, preferably chlorine.

The reaction can be carried out in the presence of solvent, preferably an anhydrous organic solvent, typically a hydrocarbon, such as hexane, toluene; petroleum ether; an ether, such as tetrahydrofuran, dioxane, diethyl ether, methyl-tbutyl ether; a chlorinated solvent, such as dichloromethane, dichloroethane, tetrachloroethylene, chlorobenzene or dichlorobenzene; or a mixture of two or more, preferably two or three, of said solvents. The reaction is preferably carried out in an ether solvent, in particular tetrahydrofuran or methyl-tbutyl ether.

The stoichiometric ratio of p-tolyloxy benzyl ether of formula (VI) to metallating agent approx. may range from 0.5 to 10. preferably from 1 to 1.5. The reaction can be carried out at a temperature approx. ranging from −80° C. to 10° C., preferably from −15° C. to 0° C.

The stoichiometric ratio of amine of formula (VII) to the salt derivative of p-tolyloxy benzyl ether of formula (VIa) may range from 0.5 to 10, preferably from 1 to 1.5. The reaction can be carried out at a temperature approx. ranging from −80° C. to the reflux temperature of the reaction mixture, preferably from 25° C. to 50° C.

A compound of formula (II), wherein X is =CO and R is —N(isopropyl)$_2$, which can optionally be isolated, can be obtained by reacting p-cresol, or a salt thereof, and a compound of formula (VIII). The reaction which can be schematized as follows is preferably carried out in the presence of a basic agent, such as sodium, potassium, lithium or calcium hydroxides; sodium or potassium carbonates; an organic tertiary amine such as triethylamine or ethyldiisopropylamine or an alkali alkoxide such as sodium methoxide or sodium ethoxide. The basic agent is preferably sodium or potassium hydroxide, or sodium ethoxide. A p-cresol salt is for instance a salt with one of the inorganic bases or organic tertiary amines mentioned above.

The stoichiometric ratio of compound of formula (VIII) to p-cresol or a salt thereof approx. may range from 0.5 to 10, preferably from 1 to 1.5.

The reaction between a compound of formula (VIII) and p-cresol or a salt thereof can optionally be carried out in the presence of solvent, for example an organic solvent or mixtures thereof with water, typically an ether, such as tetrahydrofuran, dioxane, diethyl ether; a chlorinated solvent, such as dichloromethane, dichloroethane, tetrachloroethylene, chlorobenzene or dichlorobenzene; an alkanol, such as methanol, ethanol or isopropanol, or a mixture of two or more, preferably two or three, of said solvents or with water. Particularly preferred are the reactions carried out in alcohols, more particularly in ethanol or a water/ethanol mixture.

The reaction can be carried out at a temperature approx. ranging from 0° C. to the reflux temperature of the reaction mixture, preferably from 25° C. to 50° C.

A compound of formula (II), wherein X is =CO and R is a OR$_1$, group, as defined above, which can optionally be isolated, can be obtained by reacting p-cresol, or a salt thereof, and a cinnamic acid derivative of formula (IX). The reaction, which can be schematized as follows

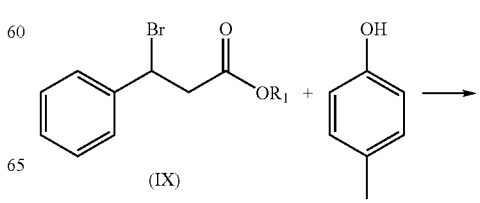

-continued

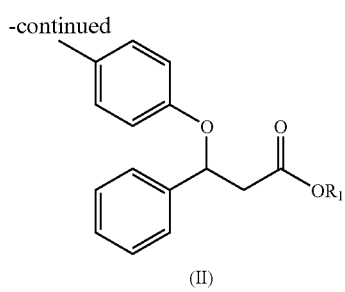

(II)

is preferably carried out in the presence of a basic agent, substantially as reported above as regards the reaction between a compound of formula (VIII) and p-creosol, or a salt thereof.

A compound of formula (III) wherein Y is hydroxy and Z is hydrogen can be prepared by reducing a compound of formula (X)

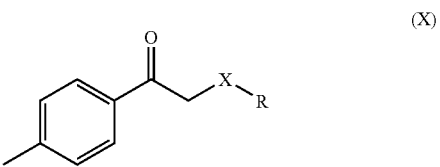

(X)

wherein X and R are as defined above, with an alkali or alkaline-earth metal borohydride, according to known methods.

A compound of formula (III) wherein Y, being as defined above, is other than hydroxy and Z is hydrogen or Y and Z, taken together complete a double bond, can be obtained from a compound of formula (III) wherein Y is hydroxy and Z is hydrogen according to known methods.

A compound of formula (X), wherein X is —$CH_2$— and R is —N(isopropyl)$_2$ can be obtained for instance according to Izvestiya Akademii Nauk SSSR, Seriya Khimicheskaya (1966), (4), 752-3. A compound of formula (X), wherein X is =CO and R is —N(isopropyl)$_2$ can be obtained for instance according to Tetrahedron Letters, ((2003) 44(43), 7957-9. A compound of formula (X), wherein X is =CO and R is —OR$_1$, wherein R$_1$ is as defined above, is a commercially available product or easily obtainable therefrom. The compounds of formula (VI), (VII), (VIII) and (IX) are usual reagents or are anyway obtainable with known methods from commercially available products.

A compound of formula (II)

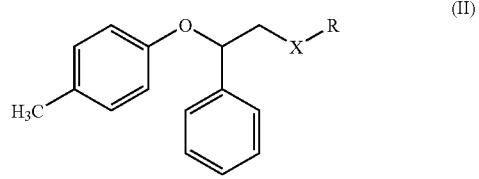

(II)

in which when X is —$CH_2$— then R is —N(isopropyl)$_2$; or when X is =CO then R is —N(isopropyl)$_2$ or —OR$_1$, wherein R$_1$ is an aryl or a straight or branched $C_1$-$C_6$ alkyl group, optionally substituted with phenyl, is a novel compound and is a further object of the present invention.

Examples of preferred compounds of formula (II) are:
diisopropyl-(3-phenyl-3-p-tolyloxy-propyl)-amine;
diisopropyl-(3-phenyl-3-p-tolyloxy-propyl)-amide; and
methyl (3-phenyl-3-p-tolyloxy)-propionate.

The following examples illustrate the invention.

EXAMPLE 1

Preparation of p-tolyloxy-benzyl ether (VI)

A three-necked round-bottom flask equipped with condenser, magnetic stirrer, thermometer, is loaded with p-cresol (100 g; 0.925 mol) and tetrahydrofuran (300 ml) under nitrogen stream. Sodium carbonate (166 g; 1.20 mol) is added, keeping the suspension under stirring. The resulting mixture is then refluxed while benzyl chloride (158.1 g; 0.925 mol) is dropped therein in 30 minutes. After 18 hours, water is added (300 ml), the phases are separated and the aqueous phase is extracted with toluene (3×200 ml). The combined organic phases are dried over sodium sulfate and evaporated to dryness. 156.1 g of p-tolyloxy-benzyl ether are obtained as a solid crude, which is dried under vacuum at 50° C.

$^1$HNMR (300 MHz, CDCl$_3$): δ (ppm) 7.49-7.31 (m, 5H), 7.12 (d, 2H,), 6.91 (d, 2H), 5.07 (s, 2H), 2.29 (s, 3H)

EXAMPLE 2

Diisopropyl-(3-phenyl-3-p-tolyloxy-propyl)-amine [(II) X is $CH_2$; R is N(isopropyl)$_2$]

A three-necked round-bottom flask equipped with condenser, magnetic stirrer, thermometer, is loaded under nitrogen stream with p-tolyloxy-benzyl ether (11.2 g; 0.0589 mol), tetramethylenediamine (6.8 g; 0.0589 mol) and tetrahydrofuran (50 ml), then cooled to 15° C. under stirring. A 2.5 M solution of butyl lithium (24 ml 0.0589 mol) in hexane is dropped therein, keeping the temperature below 0° C. After completion of the addition, temperature is kept at 0° C. for a further hour and a solution of chloroethyl diisopropylamine (9.6 g; 0.0589 mol) in tetrahydrofuran (10 ml) is added. The mixture is left to warm to room temperature, then after an hour is poured in an ammonium chloride saturated solution (50 ml), the phases are separated and the aqueous phase is extracted with toluene (3×30 ml). The combined organic phases are dried over sodium sulfate and evaporated to dryness. The resulting diisopropyl-(3-phenyl-3-p-tolyloxy-propyl)-amine is purified by flash chromatography. 9.9 g of product, as a pale yellow oil, are obtained.

$^1$HNMR (300 MHz, CDCl$_3$): δ (ppm) 7.36-7.17 (m, 5H), 6.96 (d, 2H), 6.74 (d, 2H), 5.22 (dd, 1H), 3.05 (m, 2H), 2.65 (m, 2H), 2.21 (s, 3H), 2.15-1.85 (m, 2H), 1.0 (m, 12H).

EXAMPLE 3

Tolterodine Free Base from diisopropyl-(3-phenyl-3-p-tolyloxy-propyl)-amine [from (II) wherein X is $CH_2$ and R is N(isopropyl)$_2$]

A three-necked round-bottom flask equipped with condenser, mechanical stirrer, thermometer, is loaded with diisopropyl-(3-phenyl-3-p-tolyloxy-propyl)-amine (1.0 g; 0.0031 mol) and polyphosphoric acid (16.5 g). After three hours under stirring at room temperature, the reaction is completed. The reaction mixture is poured in ice/water (10 g), alkalinized to pH 9-10 with NaOH 50% w/w and left under stirring for 30 minutes, then diluted with toluene (30 ml). The phases are separated and the aqueous phase is extracted with toluene (2×30 ml). The combined organic phases are dried over sodium sulfate and evaporated to dryness. The resulting solid is crystallized from hexane (3 ml), filtered and dried under vacuum at 50° C. in a static dryer, to obtain 0.53 g of product.

EXAMPLE 4

Preparation of diisopropyl-(3-phenyl-3-p-tolyloxy-propyl)-amide. [(II) wherein X is CO and R is N(isopropyl)$_2$]

A 1M solution of sodium ethoxide in ethanol (6.6 ml) under nitrogen pressure and cooled to 0° C., is slowly added dropwise with p-cresol (6.6 mmol, 0.72 g). After completion of the addition, the mixture is reacted for 15' at room temperature, then added dropwise with in a solution of diisopropyl-(3-phenyl-3-bromine-propyl)-amide (VIII) (6.6 mmol, 2.0 g) at room temperature checking that temperature does not exceed 30° C. The mixture is reacted for 4 h. The completion of the reaction is checked by HPLC, the mixture is acidified with acetic acid to pH 6-7 and the solvent is distilled off under reduced pressure. The resulting oil is dissolved in methylene chloride (5.0 ml) and washed with water (3×5 ml). The separated organic phase is then dried over sodium sulfate and the solvent is evaporated off under reduced pressure. The resulting pale yellow oil is purified by flash chromatography (hexane/ethyl acetate 8:2) to yield 0.5 g of product.

Following the same procedure, starting from a compound of formula (IX) in which R$_1$ is CH$_3$, methyl (3-phenyl-3-p-tolyloxy)-propionate is obtained [(II) wherein X is ═CO and R is —OCH$_3$].

EXAMPLE 5

Preparation of 3-(2-hydroxy-5-methyl-phenyl)-N,N-diisopropyl-3-phenyl-propionamide (IV) [from (II) wherein X is CO and R is N(isopropyl)$_2$]

A three-necked round-bottom flask equipped with condenser, mechanical stirrer, thermometer, is loaded with N,N-diisopropyl-3-phenyl-3-p-tolyloxy-propionamide (1.0 g; 0.0029 mol) and polyphosphoric acid (16.5 g). After four hours under stirring at room temperature the reaction is completed. The reaction mixture is poured in ice/water (10 g), alkalinized to pH 9-10 with NaOH 50% w/w and left under stirring for 30 minutes, then diluted with toluene (30 ml). The phases are separated and the aqueous phase is extracted with toluene (2×30 ml). The combined organic phases are dried over sodium sulfate and evaporated to dryness. The resulting oil is purified by flash chromatography (hexane/ethyl acetate 7:3). 0.59 g of product, as a pale yellow oil, are obtained.

EXAMPLE 6

Preparation of 3-(2-hydroxy-5-methyl-phenyl)-3-phenylpropionic acid methyl ester (V). [From (II) wherein X is CO and R is OCH$_3$]

A three-necked round-bottom flask equipped with condenser, mechanical stirrer, thermometer, is loaded with 3-p-tolyloxy-3-phenyl-propionic acid methyl ester (1.0 g; 0.0037 mol) and polyphosphoric acid (16.5 g). After four hours under stirring at room temperature the reaction is completed. The reaction mixture is poured in ice/water (10 g), alkalinized to pH 9-10 with NaOH 50% w/w and left under stirring for 30 minutes, then diluted with toluene (30 ml). The phases are separated and the aqueous phase is extracted with toluene (2×30 ml). The combined organic phases are dried over sodium sulfate and evaporated to dryness. The resulting oil is purified by flash chromatography (hexane/ethyl acetate 7:3). 0.41 g of product, as a pale yellow oil, are obtained.

EXAMPLE 7

Preparation of Tolterodine Free Base From 3-(2-hydroxy-5-methyl-phenyl)-N,N-diisopropyl-3-phenyl-propionamide (IV)

A suspension of lithium aluminium hydride (3 g, 0.08 mols) in 350 ml of anhydrous ether is added with 0.5 g of 3-(2-hydroxy-5-methyl-phenyl)-N,N-diisopropyl-3-phenyl-propionamide in portions. The mixture is refluxed while stirring for 4 days. Afterwards, water is carefully added to destroy the lithium aluminium hydride excess, the mixture is acidified to pH 5 with acetic acid, the ether phase is separated and dried over sodium sulfate. The solvent is evaporated to obtain an oil which is purified by flash chromatography (eluent hexane-ethyl acetate 7:3). 0.1 g of tolterodine free base are obtained.

EXAMPLE 8

Preparation of Tolterodine from 3-(2-hydroxy-5-methyl-phenyl)-3-phenylpropionic acid methyl ester (V)

The compound 3-(2-hydroxy-5-methyl-phenyl)-3-phenyl-propionic acid methyl ester (44 g 0.163 mol) is refluxed for 24 hours in a mixture consisting of 75 ml of methanol, 75 ml of acetone containing methyl iodide (25 g, 0.175 mol) and potassium carbonate (13.75 g, 0.1 mol). Afterwards, the solid is filtered off and the solvent is evaporated off. The residue is dissolved in ether and washed with water. The solvent is evaporated off to obtain 40 g of an oil which is redissolved in ether (75 ml) and slowly dropped in a solution of lithium aluminium hydride (5.6 g, 0.147 g) in 150 ml of anhydrous ether. The mixture is left under stirring overnight. Afterwards the lithium aluminium hydride excess is destroyed with water and 15% sodium hydroxide. The precipitate is filtered off and solvent is evaporated off to obtain 35 g of an oil corresponding to the propanol derivative. The resulting oil is dissolved in 50 ml of chloroform containing 15 ml of pyridine and the mixture is cooled to −10° C. p-Toluenesulfonyl chloride (14 g, 0.07 mols) is dropped therein and the mixture is reacted at −5/0° C. overnight, then poured in ice/water. The organic phase is separated, washed with diluted hydrochloric acid and distilled under vacuum at a temperature below 50° C. The resulting low-melting solid, that is the tosyl-derivative, is placed in autoclave together with 50 ml of acetonitrile and 50 g of diisopropylamine. After heating the mixture at 80° C. for a week, volatile solvents are evaporated off. The residue is treated with 2N sodium hydroxide and extracted with ether. The product is extracted from the ether phase with a 2N HCl solution. After further washings with ether, the acidic phase is adjusted to basic pH with sodium hydroxide and the product is re-extracted with ether. The organic solution is then evaporated to give an oil (20 g) corresponding to tolterodine phenol-protected as the methyl ether. Said oil is finally dissolved in dichloromethane (75 ml), cooled to 0° C. and treated with a 1N solution of boron tribromide in dichloromethane (32 ml 0.032 mols). The mixture is kept one week under stirring in thermocryostat at temperatures ranging from 0 to 5° C. Afterwards, the solvent is evaporated off and the residue is partitioned in a basic water/ether mixture. The organic solvent is evaporated off to obtain an oil which is purified by flash chromatography (eluent hexane-ethyl acetate 7:3) and is tolterodine free base.

EXAMPLE 9

Tolterodine Free Base from diisopropyl-(3-phenyl-3-hydroxy-propyl)-amine [from (III) wherein X is $CH_2$ and R is $N(isopropyl)_2$]

A three-necked round-bottom flask equipped with condenser, mechanical stirrer, thermometer, is loaded with diisopropyl-(3-phenyl-3-hydroxy-propyl)-amine (1.0 g; 0.0042 mol), p-cresol (0.51 g; 0.0046 mol) and 60% aqueous sulphuric acid (16.5 g). After three hours under stirring at 40° C. temperature, the reaction is completed. The reaction mixture is poured in ice/water (10 g), alkalinized to pH 9-10 with NaOH 50% w/w and left under stirring for 30 minutes, then diluted with toluene (30 ml). The phases are separated and the aqueous phase is extracted with toluene (2×30 ml). The combined organic phases are dried over sodium sulfate and evaporated to dryness. The resulting solid is crystallized from hexane (3 ml), filtered and dried under vacuum at 50° C. in a static dryer, to obtain 1.1 g of product. (yield.: 80%)

EXAMPLE 10

Preparation of 3-(2-hydroxy-5-methyl-phenyl)-N,N-diisopropyl-3-phenyl-propionamide (IV) [from (III) wherein X is CO and R is $N(isopropyl)_2$]

A three-necked round-bottom flask equipped with condenser, mechanical stirrer, thermometer, is loaded with N,N-diisopropyl-3-phenyl-3-hydroxy-propionamide (1.0 g; 0.0041 mol), p-cresol (0.48 g; 0.0044 mol) and polyphosphoric acid (16.5 g). After five hours under stirring at room temperature the reaction is completed. The reaction mixture is poured in ice/water (10 g), alkalinized to pH 9-10 with NaOH 50% w/w and left under stirring for 30 minutes, then diluted with toluene (30 ml). The phases are separated and the aqueous phase is extracted with toluene (2×30 ml). The combined organic phases are dried over sodium sulfate and evaporated to dryness. The resulting oil is purified by flash chromatography (hexane/ethyl acetate 7:3). 0.48 g of product, as a pale yellow oil, are obtained.

Analogously starting from a compound of formula (III), wherein X is =CO and R is an $—OR_1$, group as defined above, a respective compound of formula (IV) can be obtained.

EXAMPLE 11

Tolterodine Free Base from diisopropyl-(3-phenyl-3-p-tolyloxy-propyl)-amine [from (II) wherein X is $CH_2$ and R is $N(isopropyl)_2$]

A three-necked round-bottom flask equipped with condenser, mechanical stirrer, thermometer, is loaded with diisopropyl-(3-phenyl-3-p-tolyloxy-propyl)-amine (10 g; 0.031 mol) and 60% aqueous sulfuric acid (50 g). After three hours under stirring at room temperature, the reaction is completed. The reaction mixture is poured in ice/water (50 g), alkalinized to pH 9-10 with NaOH 50% w/w and left under stirring for 30 minutes, then diluted with toluene (50 ml). The phases are separated and the aqueous phase is extracted with toluene (2×50 ml). The combined organic phases are dried over sodium sulfate and evaporated to dryness. The resulting solid is crystallized from hexane (30 ml), filtered and dried under vacuum at 50° C. in a static dryer, to obtain 8.2 g of product. (yield. 82%).

The invention claimed is:
1. A compound of formula (II)

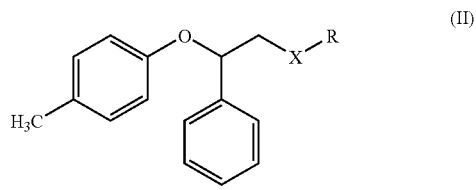

wherein X is $CH_2$ and R is $—N(isopropyl)_2$; or X is =CO and R is $—N(isopropyl)_2$ or $—OR_1$, wherein $R_1$ is an aryl or a straight or branched $C_1$-$C_6$ alkyl group, optionally substituted with phenyl.

2. The compound according to claim 1, which is selected from the group consisting of
diisopropyl-(3-phenyl-3-p-tolyloxy-propyl)-amine;
diisopropyl-(3-phenyl-3-p-tolyloxy-propyl)-amide; and
methyl (3-phenyl-3-p-tolyloxy)-propionate.

* * * * *